United States Patent [19]

Vlasuk et al.

[11] Patent Number: 5,239,058
[45] Date of Patent: Aug. 24, 1993

[54] PROTEINS HAVING ANTICOAGULANT PROPERTIES

[75] Inventors: George P. Vlasuk, Lansdale; Lloyd H. Waxman, Ottsville; Victor M. Garsky, Blue Bell; Michael P. Neeper, Wayne, all of Pa.

[73] Assignee: Merck & Co., Inc., Rahway, N.J.

[21] Appl. No.: 876,825

[22] Filed: Apr. 29, 1992

Related U.S. Application Data

[63] Continuation of Ser. No. 565,164, Aug. 13, 1990, abandoned, which is a continuation-in-part of Ser. No. 498,307, Mar. 23, 1990, abandoned, which is a continuation-in-part of Ser. No. 404,033, Sep. 7, 1989, abandoned.

[51] Int. Cl.$^5$ ................ C07K 13/00; A61K 37/02
[52] U.S. Cl. .................... 530/524; 530/334; 530/354; 530/384
[58] Field of Search ............... 530/354, 334, 384, 324; 514/12

[56] References Cited

U.S. PATENT DOCUMENTS 4,832,849  5/1989  Cardin .............................. 530/324

OTHER PUBLICATIONS

Bowie et al *Science* 247: 1306–1310 (1990).
Stewart & Young "Chemistry of SPPS" *Solid Phase Peptide Synthesis,* Pierce Chem. Co. (1984).
Vermulen, et al. Int. J. Biochem., vol. 20, No. 6, pp. 621–631 (1988).
Willadsen & Riding, Biochem. J., vol. 189, pp. 295–303 (1980).
Markwardt et al., Naturwissenschaften, vol. 45, pp. 398–399 (1958).
Markwardt et al., Naturwissenschaften, vol. 48 p. 433 (1961).
Hellmann & Hawkins, Thrombosis et Diathesis Haemorrhagica, vol. 18(3) pp. 617–62 (1967).
Ribeiro, J., J. Exp. Med. vol. 161, pp. 332–344 (1985).

*Primary Examiner*—Robert J. Hill, Jr.
*Assistant Examiner*—Shelly Guest Cermak
*Attorney, Agent, or Firm*—Charles M. Caruso; Richard S. Parr

[57] ABSTRACT

Proteins which specifically inhibit coagulation Factor Xa. The inhibitors, which do not inhibit Factor VIIa, kallikrein, trypsin, chymotrypsin, thrombin, urokinase, tissue plasminogen activator, plasmin, elastase, Factor XIa or *S. aureus* V8 protease, are polypeptides of 60 amino acid residues. The inhibitors may be purified from *Ornithodoros moubata* extract, synthesized, or produced using a recombinant DNA yeast expression system.

9 Claims, 4 Drawing Sheets

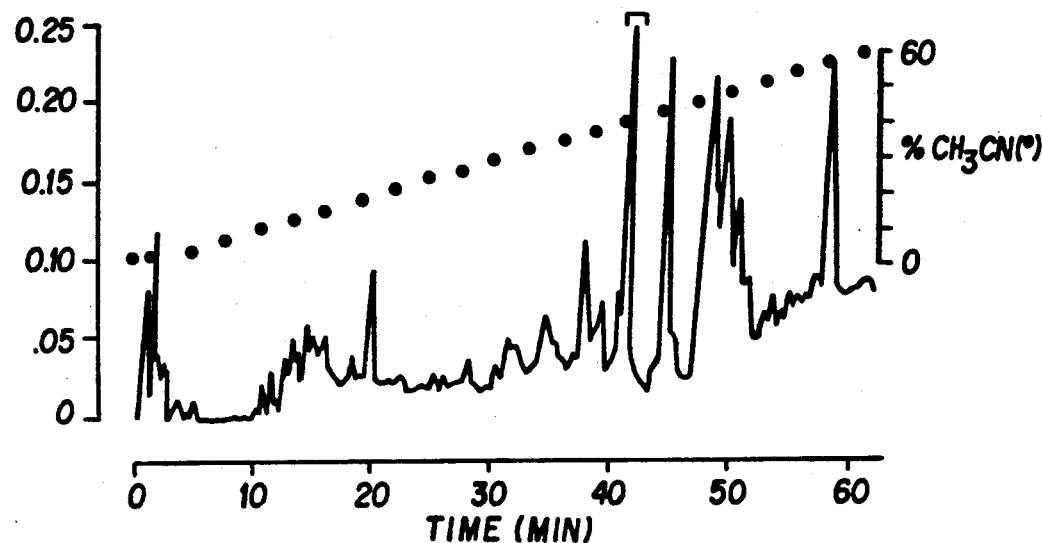
FIG. IA
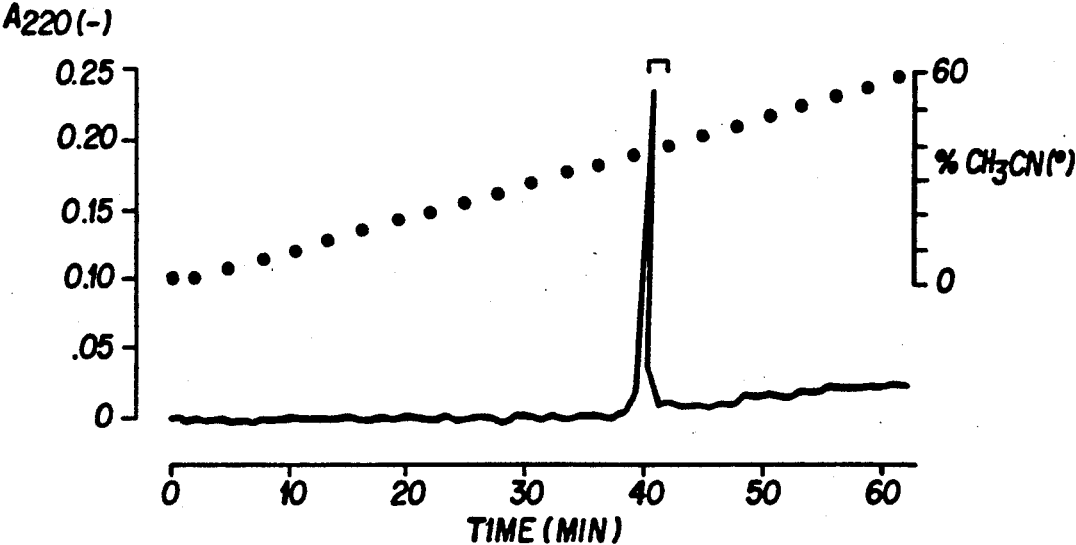
FIG. IB

PROTEINS HAVING ANTICOAGULANT PROPERTIES

This is a continuation of application Ser. No. 07/565,164, filed Aug. 13, 1990 now abandoned, continuation in part of 07/498,307 filed Mar. 23, 1990 now abandoned, continuation in part of 07/404,033 filed Sep. 7, 1989, now abandoned.

BACKGROUND OF THE INVENTION

The role of blood coagulation is to provide an insoluble fibrin matrix for consolidation and stabilization of a haemostatic plug. Formation of a cross-linked fibrin clot results from a series of biochemical interactions involving a range of well-characterized plasma proteins.

The interactions are divided into what are termed the "intrinsic pathway", in which all the substances necessary for fibrin formation are present in precursor form in circulating plasma, and the extrinsic pathway in which thromboplastin, derived from tissues, bypasses several steps in the process and accelerates clot formation. The two pathways are highly interdependent and Factor VII, Factor IX and Factor X are mutually activated (J. C. Giddings "Molecular Genetics and Immunoanalysis in Blood Coagulation" Ellis Horwood Ltd., Chichester, England 1988, p. 17).

The role of Factor X in the coagulation cascade has been reviewed by Zur et al. "Tissue factor pathways of blood coagulation", Haemostasis and Thrombosis, 1st Edition (Bloom et al., Eds) Churchill Livingstone, Edinburgh, pp. 124-139 (1981); Jackson, "The biochemistry of prothrombin activation" Haemostasis and Thrombosis, 2nd edition (Bloom et al; Eds) Churchill Livingstone, Edinburgh, pp. 165-191 (1987) and Steinberg et al. "The activation of Factor X" Haemostasis and Thrombosis, First Edition (Colman et al., Eds.) Lippincott, Philadelphia, pp. 91-111 (1982).

Human Factor X circulates in plasma as a two-chain glycoprotein with a molecular weight of about 67000 estimated by gel electrophoresis in the presence of sodium dodecylsulphate (Di Scipio et al., "A comparison of human prothrombin, Factor IX (Christmas factor), Factor X (Stuart factor) and protein S", Biochemistry, vol. 16, pp. 698-706). Slightly lower Mr values of about 59000 are obtained by sedimentation equilibrium analysis. The normal plasma concentration is about 7-10 mg per liter and the protein contains about 15% carbohydrate.

The heavy chain of Factor X, Mr=42000 demonstrates a high degree of homology with prethrombin 2 and contains the active site serine. It is covalently linked to the light chain, Mr=17000, by disulphide bridges. The light chain contains the alpha-carboxylated glutamic acid residues and shows significant homology with prothrombin fragment 1. Activation of Factor X by complexes of Factor IXa and Factor VIIIa or by tissue factor/Factor VIIa involves at least two peptide cleavages. The principal mechanism releases a small activation peptide from the heavy chain of the molecule by hydrolysis of an arginine-isoleucine bond. The active product formed in this way is termed alpha-factor Xa. This is modified further by cleavage of an arginine-glycine bond near the carboxy terminus to form $\beta$-factor Xa. Both alpha-Xa and $\beta$-Xa have the same coagulation activity.

The light chain of Factor X is unaffected by the activation process and remains linked to the heavy chain of the molecule by disulphide bridges. In this way the active substance retains the gamma-carboxyglutamic acid domains necessary for calcium-mediate attachment to phospholipid micelles or cellular surfaces. Fundamentally, therefore, in contrast to thrombin, Factor Xa remains associated with phospholipid and platelet membranes.

U.S. Pat. No. 4,588,587 describes the anticoagulant activity of Haementeria officinalis leech saliva.

Vermulen et al., Int. J. Biochem, Vol. 20, No. 6, pp. 621-31 (1988), describes the relative protease inhibition activities of tick toxins isolated from R. evertsi evertsi, B. decoloratus, B. microplus, and H. truncatum. They were found to be fast-binding or slow-binding inhibitors of trypsin and chymotrypsin.

Willadsen and Riding, Biochem J., Vol. 189, pp. 295-303 (1980), describe activity of a proteolytic-enzyme inhibitor from the ectoparasitic tick Boophilus microplus, and the effect of the inhibitor on blood-coagulation parameters.

Prior studies identified and partially purified inhibitors of Factor Xa Markwardt, F. et al. (1958) Naturwissenschaften 45, pp, 398-399 and Markwardt, F. et at. (1961) Naturwissenschaften 48 p. 433 and thrombin Hawkins, R. et al. (1967) Proceedings of the Royal Society 70 p. in tick saliva. It has been suggested that saliva contains an inhibitor of Factor IXa (Hawkins). (Hellmann, K. and Hawkins (1967) Thromb. Diath. Haemorrh. 18 pp. 617-625) Ribeiro et al. reported that tick saliva blocks clotting by inhibiting the intrinsic pathway (Ribeiro, J. (1985) J. Exp. Med. 161 pp. 332-344) but they did not identify the site of inhibition. This study also demonstrated for the first time antiplatelet activity which blocked platelet aggregation induced by ADP, collagen, or platelet activating factor (Ribeiro, J. (1985) J. Exp. Med. 161 pp. 332-344). No attempt was made to purify any of these factors to enable an analysis of their structures or mechanism of action.

The S. cerevisiae α-mating factor pre-pro leader sequence has been utilized in the expression of heterologous genes as secreted products in yeast (Brake et al., Proc. Natl. Acad. Sci. USA vol. 81, pp. 4642-4646 (1984); Miyajima et al., Gene vol. 37, pp. 155-161 (1985); Vlasuk et al., J. Biol. Chem. vol. 261, pp. 4789-4796 (1986); Schultz et al., Gene vol. 54, pp. 113-123 (1987); Schultz et al., Gene vol. 61, pp. 123-133 (1987); Bayne et al., Gene, vol. 66 pp. 235-244 (1988); and Laison et al., Biotechnology, vol. 6, pp. 72-77 (1988)). Proteins produced as fusion products are proteolytically processed by the Lys-Arg-cleaving endopeptidase (KEX2) encoded by the KEX2 gene and products are secreted into the culture medium. The KEX2 cleaves on the C-terminal side of Lys-Arg residues which are present between the ppL sequence and the heterologous gene.

SUMMARY OF THE INVENTION

The present invention includes proteins and related variants which specifically inhibit coagulation Factor Xa. The proteins are low molecular weight serine protease inhibitors. One of the proteins is a single polypeptide of 60 amino acid residues with a calculated molecular mass of 6984.9. It is highly specific for Factor Xa ($K_i = 0.58$ nM) and does not inhibit Factor VIIa, kallikrein, trypsin, chymotrypsin, thrombin, urokinase, plasmin, tissue plasminogen activator, elastase, Factor XIa or S. aureus V8 protease. The inhibitor does not require calcium. Complete amino acid sequences of these proteins were determined and compared with other inhibitors of serine proteases. They have limited homology with the Kunitz-type inhibitors. However, unlike other known inhibitors of this class, which all inhibit trypsin, it inhibits Factor Xa almost exclusively.

The present invention also includes compositions comprising a protein of the invention which inhibit Factor Xa and prevent coagulation in patients.

The present invention includes a method for obtaining a protein of the invention from *Ornithodoros moubata* tick extracts.

The present invention also includes a method for transforming yeast cells with cloned DNA fragments introduced into yeast-*E. coli* shuttle vectors and grown in *E. coli*, and expressing a secreted protein of the invention.

The present invention also includes a gene or degenerate equivalent encoding a protein of the present invention, and a method for producing the protein in *E. coli*.

The present invention also includes methods for preparing a protein of the invention by synthetic means, and for expression vectors containing an appropriate genetic sequence for preparing a protein of the invention using recombinant technology and methods for preparing recombinant inhibitor from yeast cells using the expression vectors.

The present invention also includes methods for generating protein mutants via PCR mutagenesis or Kunkel mutagenesis, thereby obtaining protein variants having Factor Xa inhibiting activity.

The present invention also includes methods for treating a patient to inhibit blood coagulation comprising administering to the patient a therapeutically effective amount of a composition of the invention.

DESCRIPTION OF THE FIGURES

FIG. 1 shows the reverse phase HPLC profiles of a human Factor Xa inhibitor of the invention (TAP-1) following ion-exchange chromatography (A) of tick extracts and rechromatography of the active peak (bracketed) (B)

DETAILED DESCRIPTION OF THE INVENTION

Figure 2:
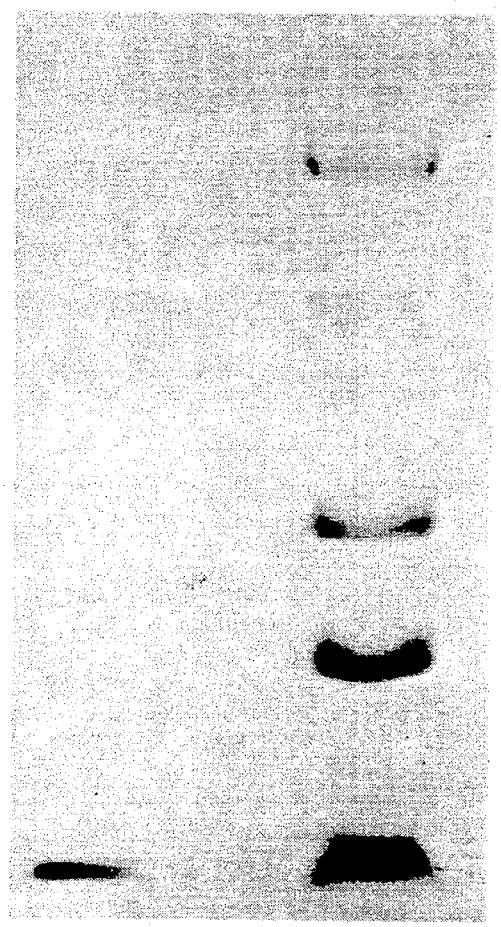
FIG. 2 shows SDS-PAGE of TAP-1 (Lane 1: inhibitor; Lane 2: molecular weight standards).

Proteins of the invention may be obtained from *Ornithodoros moubata* tick extracts, synthesized, or produced using recombinant technology. Preferred proteins of the invention have the following amino acid sequence:

$$NH_2-Tyr-Asn-Arg-Leu-Cys-Ile-Lys-Pro-AA_1-Asp-Trp-Ile^{12}-$$

$$Asp-Glu-Cys-Asp-Ser-Asn-Glu-Gly-Gly-Glu-Arg-Ala^{24}-$$

$$AA_2-Phe-Arg-Asn-AA_3-Lys-Gly-Gly-Cys-Asp-Ser-Phe^{36}-$$

$$Trp-Ile-Cys-Pro-Glu-Asp-His-Thr-Gly-Ala-Asp-Tyr^{48}-$$

$$Tyr-Ser-Ser-Tyr-AA_4-Asp-Cys-Phe-Asn-Ala-Cys-Ile^{60}-COOH$$

wherein $AA_1$, $AA_2$, $AA_3$ and $AA_4$ are Arg, Tyr, Gly and Arg respectively, (referred to hereinafter as "TAP-1") or $AA_1$, $AA_2$, $AA_3$ and $AA_4$ are Gln, Phe, Asp and Gln respectively (referred to hereinafter as "TAP-2")

Also preferred are variants of TAP-1 having one or more of the arginine amino acids at positions 9, 23, 27 and 53 replaced by asparagine, and variants of TAP-2 having one or more of the arginine amino acids at positions 23 and 27 replaced by asparagine.

Also preferred are variants of TAP-1 having aspartic acid at position 16 replaced by arginine.

Also within the present invention are bifunctional proteins having a polypeptide sequence comprising the above-described sequence having TAP-1 protein activity and included therein the tripeptide sequence arginine-glycine-aspartic acid (RGD). The presence of the RGD tripeptide is achieved, for example, by inserting glycine between amino acid positions 9 and 10, wherein $AA_1$ is arginine, or between amino acid positions 53 and 54, wherein $AA_4$ is arginine.

The bifunctional molecules are particularly suited for targeting proteins of the present invention to activated platelets where there is an assembled prothrombinase complex. The prothrombinase complex, composed of Factor Xa, Factor Va, an appropriate phospholipid surface and prothrombin, is responsible for the Factor Xa conversion of prothrombin to thrombin in vivo. The phospholipid component of this complex can be supplied by any cellular surface. However, it has been demonstrated that upon activation, platelets vesicularize into microparticles which expose Factor Va binding sites. These activated platelet micro-particles are extremely active in supporting the prothrombinase complex. Insertion of an RGD sequence in an appropriate location of a non-adhesive protein creates a protein capable of binding to integrins which recognize this peptide sequence such as the glycoprotein IIb/IIIa protein (Maeda, T. et al. (1989), *J. Biol. Chem.* 264, 15165–15168). Upon activation, the platelet IIb/IIIa complex becomes exposed and is critical in the subsequent fibrinogen-mediated aggregation. Insertion of an RGD sequence in an appropriate region of TAP (by, for example, site-specific mutagenesis) creates a bifunctional molecule targeted to activated platelets where the prothrombinase complex is assembled.

The $K_i$ for inhibition of TAP-1 is 0.58 nM.

Proteins of the present invention and their isoforms and natural variants are obtained by:

(a) homogenizing *Ornithodoros moubata* tick extracts, centrifuging the homogenate to produce supernatant protein suspension fractions and lyophilizing the fractions;

(b) dissolving the lyophilized fractions in water and applying the solution to a gel filtration chromatography column to isolate the fractions containing Factor Xa inhibitory activity; and (c) applying the fractions containing Factor Xa inhibitory activity to an anion exchange column eluted with a NaCl gradient to collect fractions which inhibit Factor Xa.

The invention encompasses all natural homologues, isoforms or genetic variants having highly specific inhibitory activity against Factor Xa such as the activity of TAP-1 and TAP-2.

Proteins

Proteins of the invention include variations on the disclosed purified protein sequence or sequences which conserve the activity of the disclosed sequence or sequences, including fragments or subunits, naturally occurring mutations, allelic variants, randomly generated artificial mutants and intentional sequence variation which conserves activity. Fragments or subunits refers to any portion of the sequence which contains fewer amino acids than the complete protein, e.g. partial sequences excluding portions at the N- and/or C-termini of the complete protein.

Proteins of the invention also include disclosed recombinant protein sequence or sequences which conserve the activity of the purified protein sequence or sequences. Also included are hybrid proteins, such as fusion proteins or proteins resulting from the expression of multiple genes within the expression vector, and may include a polypeptide having the specific activity of a disclosed protein linked by peptide bonds to a second polypeptide.

It will be understood that other variants of any of the native proteins of the present invention are included, especially any variants that differ from the isolated proteins only by conservative amino acid substitution. Conservative amino acid substitutions are defined as "sets" in Table 1 of Taylor, W. R., *J. Mol. Biol.*, Vol. 188, p. 233 (1986). The proteins or fragments thereof in this application include any such variations in the amino acid substitution, deletion, or other process, provided that the protein, after purification, immunochemically reacts with antibodies specific for the above-described inhibitor proteins.

Proteins of the invention may be prepared using solid phase synthesis, such as that described by Merrifield, *J. Am. Chem. Soc.*, 85, 2149 (1964) or other equivalent chemical syntheses known in the art such as the syntheses of Houghten, *Proc. Natl. Acal. Sci.*, 82, 5132 (1985), paying particular attention to treatment of the protein-containing solution following HF cleavage. Solid-phase synthesis is commenced from the C-terminus of the peptide by coupling a protected amino acid to a suitable resin, as generally set forth in U.S. Pat. No. 4,244,946, issued Jan. 21, 1982 to Rivier et al., the disclosure of which is hereby incorporated by reference. Examples of synthesis of this general type are set forth in U.S. Pat. Nos. 4,305,872 and 4,316,891.

In synthesizing the polypeptides, the carboxyl terminal amino acid, having its alpha-amino group suitable protected, is coupled to a chloromethylated polystyrene resin or the like. After removal of the alpha-amino protecting group, as by using trifluoroacetic acid in methylene chloride, the next step in the synthesis is ready to proceed. Other standard cleaving reagents and conditions for the removal of specific amino protecting groups may be used, as described in the open literature.

The remaining alpha-amino- and side-chain-protected amino acids are then coupled stepwise in the desired order by condensation to obtain an intermediate compound connected to the resin. As an alternative to adding each amino acid separately in the synthesis, some of them may be coupled to one another prior to the addition to the growing solid-phase chain. The selection of the appropriate coupling reagents is within the skill of the art.

The condensation between two amino acids, or an amino acid and a peptide, or a peptide and a peptide can be carried out according to the usual condensation methods such as axide method, mixed acid anhydride method, DCC (dicyclohexylcarbodiimide) method, active ester method (p-nitrophenyl ester method, BOP [benzotriazole-1-yl-oxy-tris (dimethylamino) phosphonium hexafluorophosphate] method, N-hydroxysuccinic acid imido ester method, etc), Woodward reagent K method. In the case of elongating the peptide chain in the solid phase method, the peptide is attached to an insoluble carrier at the C-terminal amino acid. For insoluble carriers, those which react with the carboxy group of the C-terminal amino acid to form a bond which is readily cleaved later, for example, halomethyl resin such as chloromethyl resin and bromomethyl resin, hydroxymethyl resin, aminomethyl resin, benzhydrylamine resin, and t-alkyloxycarbonylhydrazide resin can be used.

Common to chemical syntheses of peptides is the protection of the reactive side-chain groups of the various amino acid moieties with suitable protecting groups at that site until the group is ultimately removed after the chain has been completely assembled. Also common is the protection of the alpha-amino group on an amino acid or a fragment while that entity reacts at the carboxyl group followed by the selective removal of the alpha-amino-protecting group to allow subsequent reaction to take place at that location. Accordingly, it is common that, as a step in the synthesis, an intermediate compound is produced which includes each of the amino acid residues located in the desired sequence in the peptide chain with various of these residues having side-chain protecting groups. These protecting groups are then commonly removed substantially at the same time so as to produce the desired resultant product following purification.

The applicable protective groups for protecting the alpha- and omega-side chain amino groups are exemplified such as benzyloxycarbonyl (hereinafter abbreviated as Z), isonicotinyloxycarbonyl (iNOC), O-chlorobenzyloxycarbonyl [Z(2Cl], p-nitrobenzyloxycarbonyl [Z(NO₂], p-methoxybenzyloxycarbonyl [Z(OMe)], t-butoxycarbonyl, (Boc), t-amyloxycarbonyl (Aoc), isobornyloxycarbonyl, adamatyloxycarbonyl, 2-(4-biphenyl)-2-propyloxycarbonyl (Bpoc), 9-fluorenylmethoxycarbonyl (Fmoc), methylsulfonylethoxycarbonyl (Msc), trifluoroacetyl, phthalyl, formyl, 2-nitrophenylsulphenyl (NPS), diphenylphosphinothioyl (Ppt), dimethylphosphinothioyl (Mpt) and the like.

As protective groups for carboxy group there can be exemplified, for example, benzyl ester (OBzl), cyclohexyl ester (Chx), 4-nitrobenzyl ester (ONb), t-butyl ester (Obut), 4-pyridylmethyl ester (OPic), and the like. It is desirable that specific amino acids such as arginine, cysteine, and serine possessing a functional group other than amino and carboxyl groups are protected by a suitable protective group as occasion demands. For example, the guanidino group in arginine may be protected with nitro, p-toluenesulfonyl, benzyloxycarbonyl, adamantyloxycarbonyl, p-methoxybenzenesulfonyl, 4-methoxy-2, 6-dimethylbenzenesulfonyl (Mds), 1, 3, 5-trimethylphenysulfonyl (Mts), and the like. The thiol group in cysteine may be protected with p-methoxybenzyl, triphenylmethyl, acetylaminomethyl, ethylcarbamoyle, 4-methylbenzyl, 2, 4, 6-trimethybenzyl (Tmb) etc, and the hydroxyl group in serine can be protected with benzyl, t-butyl, acetyl, tetrahydropyranyl etc.

Stewart and Young, "Solid Phase Peptide Synthesis", Pierce Chemical Company, Rockford, Ill. (1984) provides detailed information regarding procedures for preparing peptides. Protection of $\alpha$-amino groups is described on pages 14–18, and side-chain blockage is described on pages 18–28. A table of protecting groups for amine, hydroxyl and sulfhydryl functions is provided on pages 149–151. These descriptions are hereby incorporated by reference.

After the desired amino-acid sequence has been completed, the intermediate peptide is removed from the resin support by treatment with a reagent, such as liquid HF and one or more thio-containing scavengers, which not only cleaves the peptide from the resin, but also cleaves all the remaining side-chain protecting groups. Following HF cleavage, the protein sequence is washed with ether, transferred to a large volume of dilute acetic acid, and stirred at pH adjusted to about 8.0 with ammonium hydroxide.

Preferably in order to avoid alkylation of residues in the polypeptide, (for example, alkylation of methionine, cysteine, and tyrosine residues) a thio-cresol and cresol scavenger mixture is used. The resin is washed with ether, and immediately transferred to a large volume of dilute acetic acid to solubilize and minimize intermolecular cross-linking. A 250 $\mu$M polypeptide concentration is diluted in about 2 liters of 0.1M acetic acid solution. The solution is then stirred and its pH adjusted to about 8.0 using ammonium hydroxide. Upon pH adjustment, the polypeptide takes its desired conformational arrangement.

Recombinant DNA Technology

Recombinant DNA technology may be used to produce proteins of the invention. This technology allows segments of genetic information, DNA, from different cells, and usually from different organisms, to be joined end-to-end outside the organisms from which the DNA was obtained and to incorporate this hybrid DNA into a cell that will allow the production of the protein for which the original DNA encodes. Genetic information, DNA or mRNA, is isolated and incorporated into an appropriate cloning vector, and transduced into an appropriate host cell.

Cloning vectors useful for this technology include a DNA sequence which accommodates specific experimental foreign DNA. The vectors are introduced into host cells that can exist in a stable manner and express the protein dictated by the experimental DNA. Cloning vectors may include plasmids, bacteriophage, viruses and cosmids.

Expression vectors are DNA sequences that are required for the transcription of cloned copies of genes and the translation of their mRNAs in an appropriate host. These vectors can express either procaryotic or eucaryotic genes in a variety of cells such as bacteria, yeast, insect and mammalian cells.

Proteins may also be expressed in a number of virus systems. A suitably constructed expression vector contains an origin of replication for autonomous replication in host cells, selective markers, a limited number of useful restriction enzyme sites, a high copy number, and strong promoters. Promoters are DNA sequences that direct RNA polymerase to bind to DNA and initiate RNA synthesis; strong promoters cause such initiation at high frequency. Expression vectors may include, but are not limited to cloning vectors, modified cloning vectors and specifically designed plasmids or viruses.

Expression Systems

Procaryotes most frequently are represented by various strains of $E.$ $coli$. Other microbial strains may be used, such as bacilli, e.g. $Bacillus$ $subtilis$, various species of Pseudomonas, or other bacterial strains. In such procaryotic systems, plasmid vectors which contain replication sites and control sequences derived from a species compatible with the host are used. For example, $E.$ $coli$ is typically transformed using derivatives of pBR322, a plasmid derived from an $E.$ $coli$ species by Bolivar et al., $Gene$ (1977) 2:95. Commonly used procaryotic control sequences, which are defined herein to include promoters for transcription initiation, optionally with an operator, along with ribosome binding site sequences, include such commonly used promoters as the beta-lactamase (penicillinase) and lactose (lac) promoter systems (Chang et al., $Nature$ (1977) 198:1056) and the tryptophan (Trp) promoter system (Goeddel et al., $Nucleic$ $Acids$ $Res.$ (1980) 8:4057) and the lambda-derived $P_L$ promoter and N-gene ribosome binding site (Shimatake et al., $Nature$ (1981) 292:128). However, any available promoter system compatible with procaryotes can be used.

Expression systems useful in the eucaryotic systems of the invention comprise promoters derived from appropriate eucaryotic genes. A class of promoters useful in yeast, for example, include promoters for synthesis of glycolytic enzymes, including those for 3-phosphoglycerate kinase (Hitzeman et al., $J.$ $Biol.$ $Chem.$ (1980) 255:2073). Other promoters include those from the enolase gene (Holland, M. J., et al., $J.$ $Biol.$ $Chem.$ (1981) 256:1385) or the Leu2 gene obtained from YEp13 (Broach, J., et al., $Gene$ (1978) 8:121).

Suitable mammalian promoters including the early and late promoters from SV40 (Fiers, et al., $Nature$ (1978) 273:113) or other viral promoters such as those derived from polyoma, adenovirus II, bovine papilloma virus or avian sarcoma viruses. Suitable viral and mammalian enhancers are cited above. In the event plant cells are used as an expression system, the nopaline synthesis promoter is appropriate (Depicker, A. et al., $J.$ $Mol.$ $Appl.$ $Gen.$ (1982) 1:561).

Insect cell expression systems useful for expressing the proteins include modified versions of the system described in Smith et al., U.S. Pat. No. 4,745,051. Baculovirus DNA comprising a baculovirus gene or a portion thereof which includes a promoter of the baculovirus gene is cleaved to obtain a DNA fragment containing at least the promoter. The desired product protein is prepared by infecting a susceptible host insect cell with a recombinant baculovirus expression vector wherein the expression vector is a recombinant baculovirus genome comprising at least one selected heterologous product protein polypeptide structural gene under the transcriptional control of a baculovirus polyhedrin promoter.

A recombinant baculovirus expression vector capable of expressing a selected gene in a host insect cell is produced by cleaving baculovirus DNA to produce a DNA fragment comprising a baculovirus polyhedrin promoter, and sufficient flanking DNA sequences to facilitate homologous recombination; inserting the baculovirus DNA fragment into a cloning vehicle to form a modified cloning vector; identifying a selected restriction site of the cloned baculovirus DNA fragment which is under the transcriptional control of the baculovirus polyhedrin promoter; deleting from the modified cloning vector the additional restriction site in the baculovirus DNA fragment under the transcriptional control of the baculovirus polyhedrin promoter; inserting a selected heterologous gene into the unique restriction site to form a recombinant shuttle vector; contacting the baculovirus DNA so as to effect recombination, thereby producing a mixture of recombinant and nonrecombinant baculoviruses; and isolating a recombinant baculovirus expression vector from the mixture.

Oligonucleotide Primers

Oligonucleotide primers are prepared which will hybridize to different strands of the desired sequence and at relative positions along the sequence such that an extension product synthesized from one primer, when it is separated from its template (complement), can serve as a template for extension of the other primer into a nucleic acid of defined length. The primers may be prepared using any suitable method, such as, for example, the phosphotriester and phosphodiester methods, described respectively in Narang, S. A., et al. *Meth. Enzymol.*, 68, 90 (1979) and Brown, E. L. et al., *Meth. Enzymol*, 68, 109 (1979), or automated embodiments thereof. In one such automated embodiment, diethylphosphoramidites are used as starting materials and may be synthesized as described by Beaucage et al., *Tetrahedron Letters* (1981), 22: 1859-1862. One method for synthesizing oligonucleotides on a modified solid support is described in U.S. Pat. No. 4,458,066. It is also possible to use a primer which has been isolated from a biological source (such as a restriction endonuclease digest).

Probing cDNA Libraries cDNA or genomic libraries are screened using the colony or plaque hybridization procedure. Each plate containing bacterial colonies (or recombinant phage-infected bacteria) is replicated onto duplicate nitrocellulose filter papers (S & S type BA-85) and, for bacterial colony screens, the colonies are allowed to grow at 37° C. for 14-16 hours on L agar containing 50 µg/ml Amp. The bacteria are lysed plasmid or phage and DNA fixed to the filter by sequential treatment for 5 minutes each time with 0.2N NaOH, 1.5M NaCl, then 0.5M Tris pH 7.5, 1.5M NaCl and then 2×standard saline citrate (2×SSC). Filters are air dried and baked at 80° C. for 2 hours. The duplicate filters are prehybridized at 42° C. for 6-8 hours with 10 ml per filter of DNA hybridization buffer (5×SSC, pH 7.0, 5×Denhardt's solution (polyvinyl pyrrolidine, plus Ficoll and bovine serum albumin; 1× =0.02% of each), 50 mM sodium phosphate buffer at pH 7.0, 0.2% SDS, 20 µg/ml polyU, and 50 µg/ml denatured salmon sperm DNA.

The samples are hybridized with kinased probe under conditions which depend on the stringency desired. Typical moderately stringent conditions employ a temperature of 42° C. for 24-36 hours with 1-5 ml/filter of DNA hybridization buffer containing probe. For higher stringencies, high temperatures and shorter times are employed. The filters are washed four times for 30 minutes each time at 37° C. with 2×SSC, 0.2% SDS and 50 mM sodium phosphate buffer at pH 7, then are washed twice with 2×SSC and 0.2% SDS, air dried and are autoradiographed at −70° C. for 2 to 3 days.

Polymerase Chain Reaction Amplification

Large amounts of DNA coding for the protein may be obtained using polymerase chain reaction (PCR) amplification techniques as described in Mullis et al., U.S. Pat. No. 4,800,159. The extension product of one primer, when hybridized to another primer, becomes a template for the production of the nucleic acid sequence.

The nucleic acid sequence strands are heated until they separate, in the presence of oligonucleotide primers that bind to their complementary strand at a particular site of the template. The primer template complexes act as substrate for DNA polymerase which, in performing its replication function, extends the primers. The region in common with both primer extensions, upon denaturation, serves as template for a repeated primer extension. This process is continued with a series of heating and cooling cycles, heating to separate strands, and cooling to reanneal and extend the sequences. More and more copies of the strands are generated as the cycle is repeated. Through amplification, the coding domain and any additional primer-encoded information such as restriction sites or translation signals (signal sequences, start codons and/or stop codons) is obtained.

Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site specific DNA cleavage is performed by treating with the suitable restriction enzyme (or enzymes) under conditions which are generally understood in the art, and the particulars of which are specified by the manufacturer of these commercially available restriction enzymes. See, e.g. New England Biolab s, Product Catalog. In general, about 1 µg of plasmid or DNA sequence is cleaved by one unit of enzyme in about 20 µl of buffer solution. Typically, an excess of restriction enzyme is used to ensure complete digestion of the DNA substrate. Incubation times of about 1 to 2 hours at about 37° C. are workable, although variations can be tolerated. After each incubation, protein is removed by extraction with phenol/chloroform, and may be followed by running over a Sephadex® G-50 spin column. If desired, size separation of the cleaved fragments may be performed by polyacrylamide gel or agarose gel electrophoresis using standard techniques. A general description of size separations is formed in *Methods in Enzymology* (1980)65: 499–560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 minutes at 20 to 25° C. in 50 mM Tris, pH 7.6, 50 mM NaCl, 6 mM MgCl$_2$, 6 mM DTT and 5–10 µMdNTPs. The Klenow fragment fills in 5' overhangs but removes protruding 3' single strands, even in the presence of the four dNTPs. If desired, selective repair can be performed by supplying only one of the, or selected, dNTPs within the limitations dictated by the nature of the sticky ends. After treatment with Klenow, the mixture is extracted with phenol/chloroform and ethanol precipitated followed by running over a Sephadex ® G-50 spin column. Treatment under appropriate conditions with S1 nuclease results in hydrolysis of any single-stranded portion.

As mentioned above, oligonucleotides may be prepared by the triester method of Matteucci, et al. (*J. Am. Chem. Soc.* (1981) 103:3185) or using commercially available automated oligonucleotide synthesizers. Kinasing of single strands prior to annealing or for labelling is achieved using an excess, e.g., approximately 10 units of polynucleotide kinase to 0.1 nmole substrate in the Presence of 50 mM Tris, pH 7.6, 10 mM MgCl$_2$, 5 mM dithiothreitol, 1–2 mM ATP, 1.7 pmoles $^{32}$P-ATP(2.9 mCi/mmole), 0.1 mM spermidine, 0.1 mM EDTA Ligations are performed in 15–30 µl volumes under the following standard conditions and temperatures: 20 mM Tris-HCl, pH 7.5, 10 mM MgCl$_2$, 10 mM DTT, 33 µg/ml BSA, 10 mM–50 mM NaCl, and 1 mM ATP, 0.3–0.6 (Weiss) units T4 DNA ligase at 14° C. (for "blunt end" ligation). Intermolecular "sticky end" ligations are usually performed at 33–100 µg/ml total DNA concentrations (5–100 nM total end concentration). Intermolecular blunt end ligations (usually employing a 10–30 fold molar excess of linkers) are performed at 1 µM total ends concentration.

In vector construction employing "vector fragments," the vector fragment is commonly treated with bacterial alkaline phosphatase (BAP) in order to remove the 5' phosphate and prevent religation of the vector. BAP digestions are conducted at pH 8 in approximately 150 mM Tris, in the presence of Na$^+$ and Mg$^{2+}$ using about 1 unit of BAP per µg of vector at 60° C. for about 1 hour. In order to recover the nucleic acid fragments, the preparation is extracted with phenol/chloroform and ethanol precipitated and desalted by application to a Sephadex ® G-50 spin column. Alternatively, religation can be prevented in vectors which have been double digested by additional restriction enzyme digestion of the unwanted fragments.

For portions of vectors derived from cDNA or genomic DNA which require sequence modifications, site specific primer directed mutagenesis is used. This is conducted using a primer synthetic oligonucleotide complementary to a single stranded plasmid or phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are hybridized with kinased synthetic primer at a temperature which permits hybridization of an exact match, but at which the mismatches with the original strand are sufficient to prevent hybridization. Plaques which hybridize with the probe are then picked, cultured, and the DNA recovered.

Verification of Construction

In the constructions set forth below, correct ligations for plasmid construction are confirmed by first transforming *E. coli* strain MM294 obtained from *E. coli* Genetic Stock Center, CGSC #6135, or other suitable host with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B., et al, *Proc. Natl. Acad. Sci. USA* (1969) 62:1159, optionally following chloramphenicol amplification (Clewell, D. B., *J. Bacteriol* (1972) 110:667). The isolated DNA is analyzed by restriction and/or sequenced by the dideoxy method of Sanger, F., et al, *Proc. Natl. Acad. Sci. USA* (1977) 74:5463 as further described by Messing, et al, *Nucleic Acids Res* (1981) 9:309, or by the method of Maxam, et al, *Methods in Enzymology* (1980) 65:499.

Transformation

Depending on the host cell used, transformation is done using standard techniques appropriate to such cells. The calcium treatment employing calcium chloride, as described by Cohen, S.N., *Proc. Natl. Acad. Sci. USA* (1972) 69:2110, or the RbCl method described in Maniatis et al., *Molecular Cloning: A Laboratory Manual* (1982) Cold Spring Harbor Press, p. 254 is used for procaryotes or other cells which contain substantial cell wall barriers. Infection with *Agrobacterium tumefaciens* (Shaw, C. H., et al., *Gene* (1983) 23:315) is used for certain plant cells. For mammalian cells without such cell walls, the calcium phosphate precipitation method of Graham and van der Eb, *Virology* (1978) 52:546 is preferred. Transformations into yeast are carried out according to the method of Van Solingen, P., et al., *J. Bacter.* (1977) 130:946 and Hsiao, C. L. et al., *Proc. Natl. Acad. Sci. USA* (1979) 76:3829.

A synthetic gene coding for the inhibitor was made using oligonucleotides. The synthetic gene was fused to cheY to make a fusion protein in *E. coli*, and also fused to ompA signal peptide for secretion of the protein into the *E. coli* periplasm.

EXAMPLE 1

*Ornithodoros moubata* ticks were obtained from South Africa through Antibody Associates, Inc. (Bedford, Tex.). Colorimetric substrates were purchased from Helena Labs, American Diagnostica, and Chemical Dynamics. Human Factor Xa was from Enzyme Research Laboratories. Human plasmin, urokinase, and bovine thrombin were from Calbiochem; bovine trypsin, chymotrypsin, and pancreatic elastase were from Worthington Enzymes, Inc. Plasma kallikrein, carboxypeptidase Y, *S. aureus* V8 protease and protease inhibitors were from Sigma. Two chain tPA was from American Diagnostica.

Preparation of Crude Extracts

Fifty ticks (0.8 g) were homogenized in a ground glass homogenizer in 3 ml 20 mM Bis-Tris (pH 7.0) containing 0.15M NaCl and 50 uM E-64, 50 uM pepstatin, and 50 uM chymostatin. The homogenate was centrifuged 30 min. at 30,000×g and the resultant pellet was resuspended in 3 ml buffer and recentrifuged. The supernatants were combined, sucrose was added to a final concentration of 10 mg/ml and the extract was lyophilized. This material was dissolved in 2 ml of $H_2O$ and applied to a column of Sephadex G-75 superfine (Pharmacia) (1.5 cm×95 cm) equilibrated in 20 mM Bis-Tris-HCl (pH 7.4) containing 25 mM NaCl and 0.1 mM EDTA. Two ml fractions were collected and aliquots from selected fractions were assayed for their effect on Factor Xa and thrombin.

Purification of the Inhibitor of Factor Xa

After gel filtration, the fractions containing Factor Xa inhibitory activity were pooled and applied to a column of Mono Q (Pharmacia) (0.5×5 cm) equilibrated in 20 mM Bis-Tris-HCl (pH 6.0). The column was eluted with a gradient of NaCl (0 to 1M NaCl; 60 ml total), and 1 ml fractions were collected. The fractions which inhibited Factor Xa were dialyzed to remove salt and lyophilized. This material was dissolved in 2 ml of $H_2O$ and was applied to a Vydac $C_{18}$ column. (4.6×200 mm) equilibrated in 0.1% trifluoroacetic acid. The proteins were eluted with a linear gradient of acetonitrile (0 to 60%) in 0.1% trifluoroacetic acid at 1% per min. One ml fractions were collected and the solvents removed under vacuum. Fractions were dissolved in 0.5 ml 20 mM Tris-HCl (pH 7.4)/.15M NaCl (TBS) and assayed. Those containing inhibitory activity were pooled and rechromatographed on the same column with a convex gradient of increasing acetonitrile (0 to 40%). The peaks were collected by hand and dried down.

A crude soluble extract of whole ticks was fractionated by gel filtration on Sephadex G-75. When selected column fractions were assayed for their ability to inhibit Factor Xa, one peak was found which eluted with an apparent molecular weight of 8,000–10,000.

The peak of Factor Xa inhibitory activity was pooled and applied directly to a column of Mono Q. The inhibitor eluted in one peak of 0.25M NaCl. In an earlier attempt to purify this inhibitor a second peak of activity was found which eluted at a lower ionic strength. It was purified by similar procedures (see below).

This material was dialyzed to remove salt and lyophilized. After redissolving in a small volume of $H_2O$, aliquots were fractionated by reverse phase HPLC. The inhibitory activity eluted in one peak (FIG. 1A). This material was rechromatographed to obtain a homogeneous peak of protein (FIG. 1B). We estimate that 200–250 ug of the purified inhibitor could be obtained from 500 ticks. On SDS-PAGE one band of protein was found which had an estimated $M_r=6000$ (FIG. 2).

Other Techniques

Protein was estimated by the Lowry procedure using bovine serum albumin as a standard. SDS-PAGE was carried out on slab gels containing 16% acrylamide and 0.5% bisacrylamide. Pre-stained molecular weight standards were obtained from BRL. Proteins were detected by staining with Coomassie blue.

Enzyme Assays

Assays were carried out at room temperature in 96-well microtiter plates. The color developed from the hydrolysis of peptide-nitroanilide substrates was monitored continuously at 405 nM on a $V_{max}$ machine (Molecular Devices). The concentration of Factor Xa was determined by active site titration. The concentrations of working solutions of the other proteases were determined spectrophotometrically using published extinction coefficients. The concentration of purified inhibitor was determined by quantitative amino acid analysis. Typically, the assay included 500 pM proteolytic enzyme, 20 mM Tris-HCl (pH 7.4), 0.15M NaCl, 0.2–0.3 mM substrate and an aliquot of selected column fractions or the purified inhibitor in a total volume of 200–220 ul. In the case of human Factor Xa, the buffers also included 0.1% BSA; for S. aureus V8 protease the buffer was 50 mM $NH_4HCo_3$. The substrates used were: Spectrozyme Xa (Factor Xa), S-2238 (thrombin), S-2356 (chymotrypsin), S-2366 (Factor XIa) Boc-AlaAla-Pro-Ala-pNA (elastase), Spectrozyme Pkal (kallikrein), Spectrozyme PL (plasmin), Spectrozyme UK (urokinase) Z-Phe-Leu-Glu-pNA (S. aureus V8 protease) and Spectrozyme tPA for tPA. Factor VIIa was assayed by measuring the release of the $^3H$-activation peptide from human Factor X. For kinetic analyses, assays were carried for up to 10 min. followed by estimation of the initial rate where less than 5% of the added substrate was utilized.

Structure Determination

Prior to digestion with proteases or sequence analysis, the inhibitor was denatured by incubating for 1 hour at 37° C. in 6M guanidine hydrochloride containing 50 mM dithiothreitol, 0.25M Tris-HCl (pH 8.2) and 1 mM EDTA. Iodoacetamide was added to a final concentration of 0.1M and the mixture was allowed to stand at room temperature for 30 min. to block the sulfhydryl groups. The protein was reisolated by applying the reaction mixture directly to a Vydac $C_{18}$ column and eluting it with a gradient of acetonitrile in 0.1% trifluoroacetic acid. The protein was dried down under vacuum and sequenced directly on an Applied Biosystems gas phase sequenator.

The reduced and alkylated inhibitor was dissolved in 100 ul 50 mM $NH_4HCO_3$ and incubated at room temperature with trypsin (50:1, w/w). After 4 hours, the same amount of trypsin was added and the reaction was allowed to proceed overnight. The mixture was then applied directly to a $C_{18}$ column to fractionate the digestion products. Proteolysis by S. aureus V8 protease was carried out similarly except that the buffer was 50 mM ammonium acetate. The peaks were collected by hand and submitted for sequence analysis.

After reduction and carboxyamidomethylation, the inhibitor was sequenced directly. As shown in Table I, the sequence of the first 53 residues was determined in this way, although the identity of several amino acids was ambiguous. To extend this sequence, reduced and alkylated protein was treated with trypsin and the fragments separated by reverse phase HPLC. The polypeptides sequence was found to be the sequence of TAP-1.

TABLE I

NH₂-Terminal Sequence of RCM Inhibitor

| Cycle No. | PTH Amino Acid | Yield (pmol) |
|---|---|---|
| 1 | Tyr | 488 |
| 2 | Asn | 565 |
| 3 | Arg | 202 |
| 4 | Leu | 891 |
| 5 | Cm—Cys | 461 |
| 6 | Ile | 655 |
| 7 | Lys | 426 |
| 8 | Pro | 415 |
| 9 | Arg | 247 |
| 10 | Asp | 326 |
| 11 | Trp | 149 |
| 12 | Ile | 368 |
| 13 | Asp | |
| 14 | Glu | |
| 15 | Cm—Cys | |
| 16 | Asp | |
| 17 | Ser | |
| 18 | Asn | |
| 19 | Glu | |
| 20 | Gly | |
| 21 | Gly | |
| 22 | Glu | |
| 23 | Arg | |
| 24 | Ala | |
| 25 | Tyr | |
| 26 | Phe | |
| 27 | Arg | |
| 28 | Asn | |
| 29 | Gly | |
| 30 | Lys | |
| 31 | Gly | |
| 32 | Gly | |
| 33 | Cm—Cys | |
| 34 | Asp | |
| 35 | Ser | |
| 36 | Phe | |
| 37 | Trp | |
| 38 | Ile | |
| 39 | Cm—Cys | |
| 40 | Pro | |
| 41 | Glu | |
| 42 | Asp | |
| 43 | Ala/His | |
| 44 | Thr | |
| 45 | Gly | |
| 46 | Ala | |
| 47 | Asp | |
| 48 | Tyr | |
| 49 | Tyr | |
| 50 | Ser | |
| 51 | Ser | |
| 52 | — | |
| 53 | Arg | |

Approximate yields of phenylthiohydantoin derivatives were calculated from peak areas on the HPLC.

EXAMPLE 2

Following a procedure similar to the procedure of Example 1, and using *Ornithodoros moubata* ticks obtained from a warthog burrow near Lake Victoria, Zimbabwe, (subspecies porcinus Walton) another polypeptide sequence having Factor Xa inhibitor activity such as that of TAP-1 was determined. The other polypeptide was identified as TAP-2.

EXAMPLE 3

Starting with Boc-Ile-O-Pam resin, the alpha-amino Boc protecting group (tert-butylcarbonyl) is removed using trifluoracetic acid and methylene chloride, and the deprotected isoleucine neutralized with diisopropylethyl amine. Boc-protected Cys (PMB) (where cysteine is protected by p-methoxybenzyl) is then coupled to isoleucine mediated by dicyclohexylcarbodiimide, and deprotected with trifluoroacetic acid and methylene chloride (protocol for Applied Biosystems Inc. peptide synthesizer). Cys is then neutralized with diisopropylethylamine. Following this stepwise procedure of coupling with dicyclohexylcarbodiimide, deprotection with trifluoroacetic acid and methylene chloride, and neutralization with diisopropylethylamine, Boc-protected Ala, Asn and the remaining 56 amino acids of the 60 amino acid polypeptide are coupled in succession. The various amino acids may be suitably protected in accordance with the usual peptide synthesis practice which is well known to those skilled in the art.

Cleavage of the peptide from the resin is achieved using HF/anisole (9:1(v/v)). To avoid alkylation of cysteine and tyrosine residues, a thio-cresol and cresol scavenger mixture was used. The resin is washed with ether, and 250 μM polypeptide concentration is immediately diluted in about 2 liters of 0.1M acetic acid solution. The solution is then stirred and its pH adjusted to about 8.0 using ammonium hydroxide. Purification is conducted using preparative HPLC in 0.1% TFA $H_2O$-$CH_3CN$ gradient.

The finished amino acid sequence of the inhibitor is:

$NH_2$—Tyr—Asn—Arg—Leu—Cys—Ile—Lys—Pro—

12
                            —Arg—Asp—Trp—Ile—

Asp—Glu—Cys—Asp—Ser—Asn—Glu—Gly—Gly—

24
                                  —Glu—Arg—Ala—

Tyr—Phe—Arg—Asn—Gly—Lys—Gly—Gly—Cys—

36
                                 Asp—Ser—Phe—

Trp—Ile—Cys—Pro—Glu—Asp—His—Thr—Gly—

48
                                 —Ala—Asp—Tyr—

Tyr—Ser—Ser—Tyr—Arg—Asp—Cys—Phe—Asn—

60
                             —Ala—Cys—Ile—COOH

Inhibitory Activities of TAP-1 on Various Proteases

Figure 3:
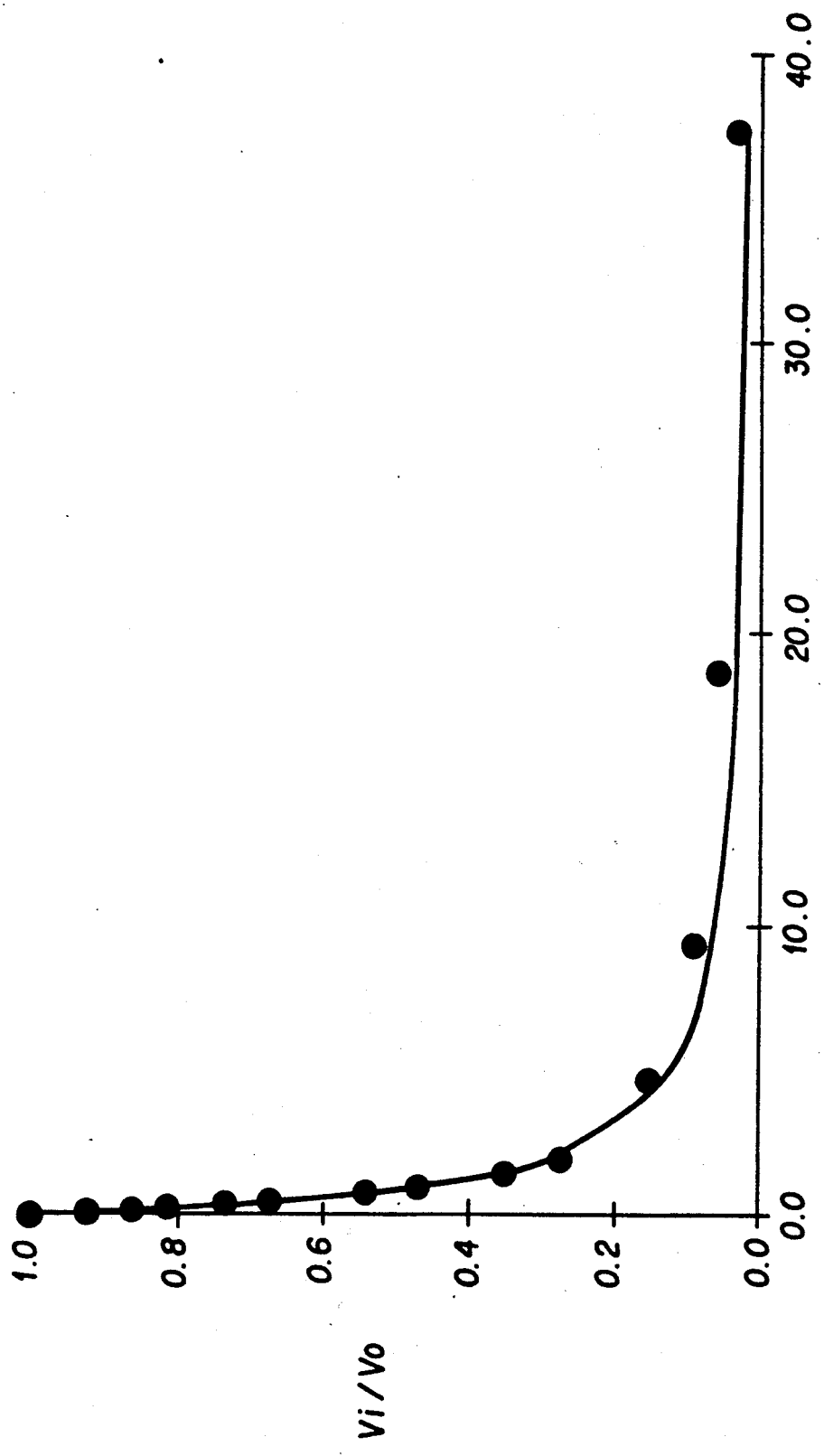
FIG. 3 shows the effect of increasing amounts of TAP-1 on the rate of initial velocities in the presence (Vi) and absence (Vo) of TAP-1 following preincubation of TAP-1 with human Factor Xa in the absence of substrate.

FIG. 3 shows the effect of increasing amounts of inhibitor on the ratio of the initial velocities in the presence (Vi) and absence (Vo) of TAP-1. Because the TAP-1 was pre-incubated with the human Factor Xa to establish equilibrium in the absence of substrate, a value for the intrinsic $K_i$ irrespective of the mechanism was calculated (solid line) using the equation for tight binding inhibition described in the article by Morrison, J. F. in *Biochem. Biophys.* Acta 185,269 (1969). The effect on TAP-1 on various proteases also was tested. At a 300-fold molar excess of TAP-1 over each protease, no inhibition of Factor VIIa thrombin, chymotrypsin, elastase, trypsin, kallikrein, urokinase, plasmin, or S. aureus V8 protease was detected. The $K_i$ was 0.58 nM. The inclusion of 1-5 mM $Ca^{++}$ had no effect on the ability of TAP-1 to inhibit Factor Xa. The effect of TAP-1 on clotting time in the presence of prothrombin, activated partial thromboplastin and modified stypven is shown in Table II.

TABLE II

Effect of TAP-1 on Various
Plasma Based Clotting Assays

| | Clotting Time (Sec.) |
|---|---|
| Prothrombin Time (Normal Human Plasma) | |
| - (control) | 14.1 |
| - (control) | 15.1 |
| 1.15 pMol | 15.1 |
| 28.9 pMol | 28.9 |
| 57.8 pMol | 31.2 |
| 115 pMol | 48.7 |
| Activated Partial Thromboplastin Time (Normal Human Plasma) | |
| - (control) | 32.6 |
| - (control) | 29.6 |
| - (control) | 31.6 |
| 28.9 pMol | 45.2 |
| 57.8 pMol | 57.7 |
| 115 pMol | 92.2 |
| Modified Stypven Time (Normal Human Plasma) | |
| - (control) | 10.1 |
| - (control) | 10.6 |
| 28.9 pMol | 17.7 |
| 57.8 pMol | 31.2 |
| 115 pMol | 65.1 |

The potential exists, in the use of recombinant DNA technology, for the preparation of various derivatives of proteins of the present invention, variously modified by resultant single or multiple amino acid substitutions, deletions, additions or replacements, for example, by means of site directed mutagenesis of the underlying DNA. All such allelic variations and modifications resulting in these derivatives are included within the scope of this invention so long as the essential, characteristic Factor Xa inhibitory activity of these proteins remains unaffected in kind. The proteins are prepared (1) having methionine as its first amino acid (present by virtue of the ATG start signal codon insertion in front of the structural gene) or (2) where the methionine is intra-or extracellularly cleaved, having its normally first amino acid, or (3) together with either its signal polypeptide or a conjugated protein other than the conventional signal polypeptide, the signal polypeptide or conjugate being specifically cleavable in an intra- or extracellular environment (see British Patent Application Publication No. 2,007,676A), or (4) by direct expression in mature form without the necessity of cleav-ing away any extraneous, superfluous polypeptide. The latter is particularly important where a given host may not, or not efficiently, remove a signal peptide where the expression vehicle is designed to express the protein together with its signal peptide. In any event, the thus produced protein, in its various forms, is recovered and purified to a level fitting it for use in inhibiting Factor Xa.

Exemplified below is a recombinant technique for producing the inhibitor in naturally folded and biologically active form.

EXAMPLE 4

Expression of the Inhibitor in Yeast

A recombinant gene encoding the inhibitor was synthesized and constructed based on the primary amino acid sequence of TAP-1. The properly modified synthetic gene was inserted into a yeast expression vector that allows for secretory expression. Yeast cells were transformed with the vector containing the synthetic gene.

Because the amino acid sequence of TAP-1 was identified, appropriately chosen synthetic oligonucleotides were used to construct the gene encoding the inhibitor. Eight oligonucleotides were synthesized, and the synthetic gene constructed by annealing and ligation.

| | |
|---|---|
| 5' TCGAATTCATGTACAACCGTCTGTGCATCAAACCGCGTGACTGGA 3'<br>45-mer | I |
| 5' TCGTCGATCCAGTCACGCGGTTTGATGCACAGACGGTTGTACATGAATTCGA 3'<br>52-mer | II |
| 5' TCGACGAATGCGACTCCAACGAAGGTGGTGAACGTGCTTACTTCCGTAACG 3'<br>51-mer | III |
| 5' CTTTACCGTTACGGAAGTAAGCACGTTCACCACCTTCGTTGGAGTCGCAT 3'<br>50-mer | IV |
| 5' GTAAAGGTGGTTGCGACTCCTTCTGGATCTGCCCGGAAGACCACACCGGTGC 3'<br>52-mer | V |
| 5' TAGTCAGCACCGGTGTGGTCTTCCGGGCAGATCCAGAAGGAGTCGCAACCAC 3'<br>52-mer | VI |
| 5' TGACTACTACTCCTCCTACCGTGACTGCTTCAACGCTTGCATCTAAGCTTGAATTCAT 3'<br>58-mer | VII |
| 5' ATGAATTCAAGCTTAGATGCAAGCGTTGAAGCAGTCACGGTAGGAGGAGTAG 3'<br>52-mer | VIII |

Each oligonucleotide was purified by electrophoresis on a 15% polyacrylamide gel, isolation and electroelution. Oligonucleotides II through VII were treated with polynucleotide kinase and annealed in complementary pairs (III and IV) and (V and VI). Oligonucleotides I and VIII were annealed directly with kinased II and VII respectively. The oligonucleotides were annealed in kinase reaction buffer by heating to 80° C. for two minutes and slow cooling over the course of an hour. The four annealed oligonucleotide pairs were pooled and treated with T4 ligase. The resulting product was digested with EcoRI. The product, representing the synthetic gene, was isolated as a 200 bp fragment after electrophoresis of the mixture on a 2% agarose gel, the identified fragment excised and electroeluted.

The DNA fragment representing the synthetic gene was ligated to pJC264 (Gan, Z.-R. et al. (1989) *Gene* 79:159–166) which had been previously digested with EcoRI and treated with alkaline phosphatase to yield plasmid 276-2E. The ligation mixture was used to transform competent *E. coli* (JM109 available from Stratagene, Calif., U.S.A.) Ampicillin resistant cells were obtained and selected for on ampicillin plates. The correct insert sequence in resulting plasmid clones was confirmed by DNA sequence analysis.

The strategy used to assemble this synthetic gene is given below. In addition, the resulting open reading frame and its translation is presented.

Construction of pKH4α2

Construction of pKH4 is described in Schultz, et al., *Gene* 61 (1987) 123–133, which is incorporated by reference. The plasmid pJC197 (Schultz et al. *Gene* 54 (1987) 113–123) is an *E. coli-S. cerevisiae* shuttle vector which contains a unique BamHI cloning site between the yeast MFα1 pre-pro leader and transcriptional terminator, originally derived in Kurjan and Herskowitz (1982)

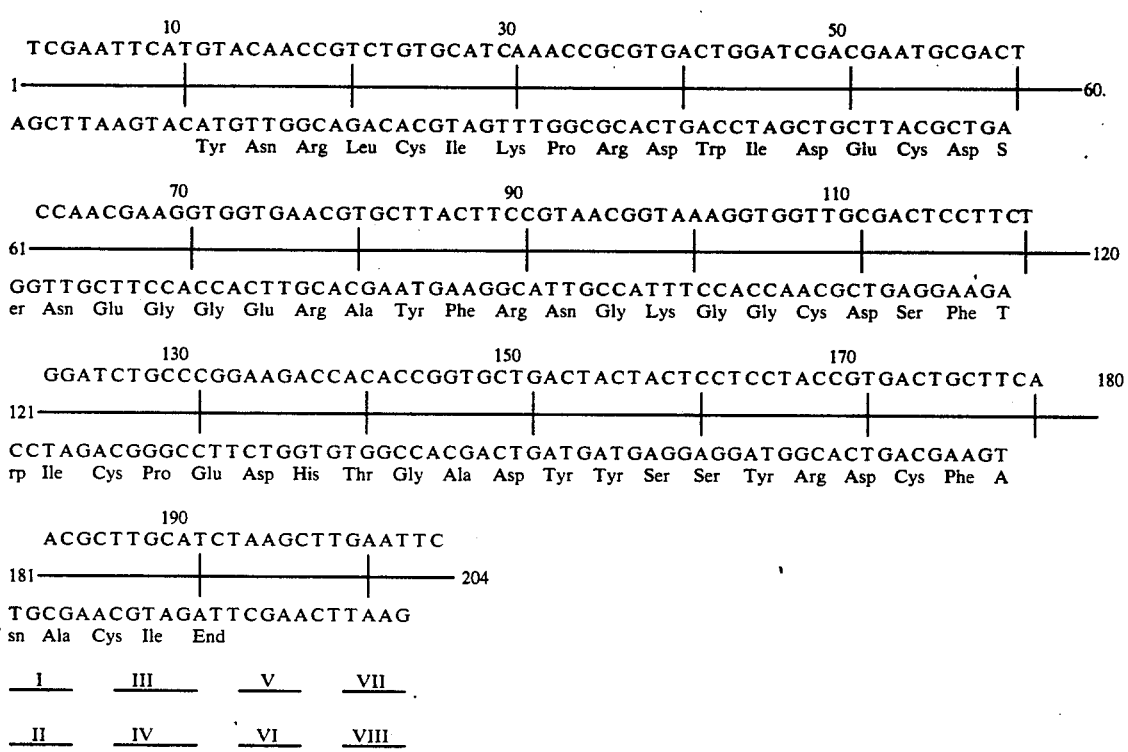

The synthetic gene was inserted into the yeast expression vector in the following manner. One plasmid, 276-2E, was selected, and a polymerase chain reaction product was obtained in a reaction using the oligonucleotide primers:

5' TAG GAT CCT CTC TTT GGA CAA GAG GTA CAA CCG TCT GTG CAT CAA ACC 3'     IX

5' ACT GGA TCC GAA TTC AAG CTT AGA TGC AAG CGT 3'     X

The inhibitor DNA was subjected to polymerase chain reaction (PCR) -effected amplification (see U.S. Pat. No. 4,800,159, column 2, lines 36–68, column 3, column 4, and column 5, lines 1–20, hereby incorporated by reference). The DNA strands were heat denatured in the presence of primers that bind to each strand. The primers instructed DNA polymerase, which performs its replication function, to copy a particular portion of the strand. The process was continued with a series of heating and cooling cycles, heating to separate strands, and cooling to allow annealing and primer extension forming copies of the desired sequences. The cycles were repeated to generate more and more copies of the specific sequences. Through amplification, the coding domain to which terminal restriction sites are appended was obtained.

The PCR product was used to generate pKH4•TAP.

ibid. pJC197 was digested with EcoRI+PstI, and the 0.7-kb PstI-EcoRI fragment containing a portion of the MFα1 pre-pro-leader, a three-frame translational terminator, and MFα1 transcriptional terminator, was gel-purified. GAL10p was isolated from YEP51 by digestion with Sau3A, flush-ending with PolIk, ligating with octameric BamHI linkers, and digestion with SalI.

The resulting 0.5-kb BamHI-SalI fragment bearing GAL10p was gel purified and ligated to a 35-bp SalI-PstI synthetic oligodeoxynucleotide adapter encoding the first 11 bp of the MFα1 nontranslated leader plus the ATG and first 8 aa of the MFα1 pre-pro-leader. The resulting 0.5-kb fragment was digested with BamHI, gel-purified, and ligated together with the aforementioned 0.7-kb PstI-EcoRI fragment plus the 4.0 kb EcoRI-BamHI vector fragment derived from pBR322. The resulting plasmid, pKH207-1, contains GAL10p fused to the MFα1 pre-pro-leader plus BamHI cloning site, translational termination codons, and MFα1 transcriptional terminator. Upon digestion with EcoRI and partial digestion with BamHI, an expression cassette of GAL10p fused to the yeast MFα1 pre-pro-leader, a unique BamHI cloning site, translational termination codons in all three reading frames, and MFα1 transcriptional terminator sequence was inserted into the yeast shuttle vector pCl/1 (Rosenberg et al. Nature 312 (1984) 77-80) which contains the yeast 2μ DNA sequence for stable propagation of the plasmid in yeast at high copy number, to form pKH4.

A 213-bp BamHI-PstI fragment encoding aa 9-79 of the ppL was prepared from the plasmid pα2 (Bayne et al., Gene 66 (1988) 235-244). The plasmid pα2 contains a portion of the yeast MFα1 pre-pro sequence (79aa) modified at codons 80 and 81 to create a BamHI site 6 aa upstream from the KEX2 processing site. The region corresponding to codon 9 (PstI) of the ppL to the BamHI site of pKH4 was removed from pKH4 after digestion with BamHI followed by partial digestion with PstI. The modified vector, pKH4α2 was prepared by replacement of this excised sequence with the BamHI-PstI fragment from pα2. Plasmid pKH4α2 contains the yeast GAL10 promoter, a portion of the MFα1 pre-pro leader (79 aa), a three-frame translational terminator and MFα1 transcriptional terminator, the yeast LEU2 gene, yeast 2μ sequences, pBR322 derived sequences, including the Ap$^R$ gene and the origin of DNA replication (ori).

Construction of pKH4•TAP

Figure 4:
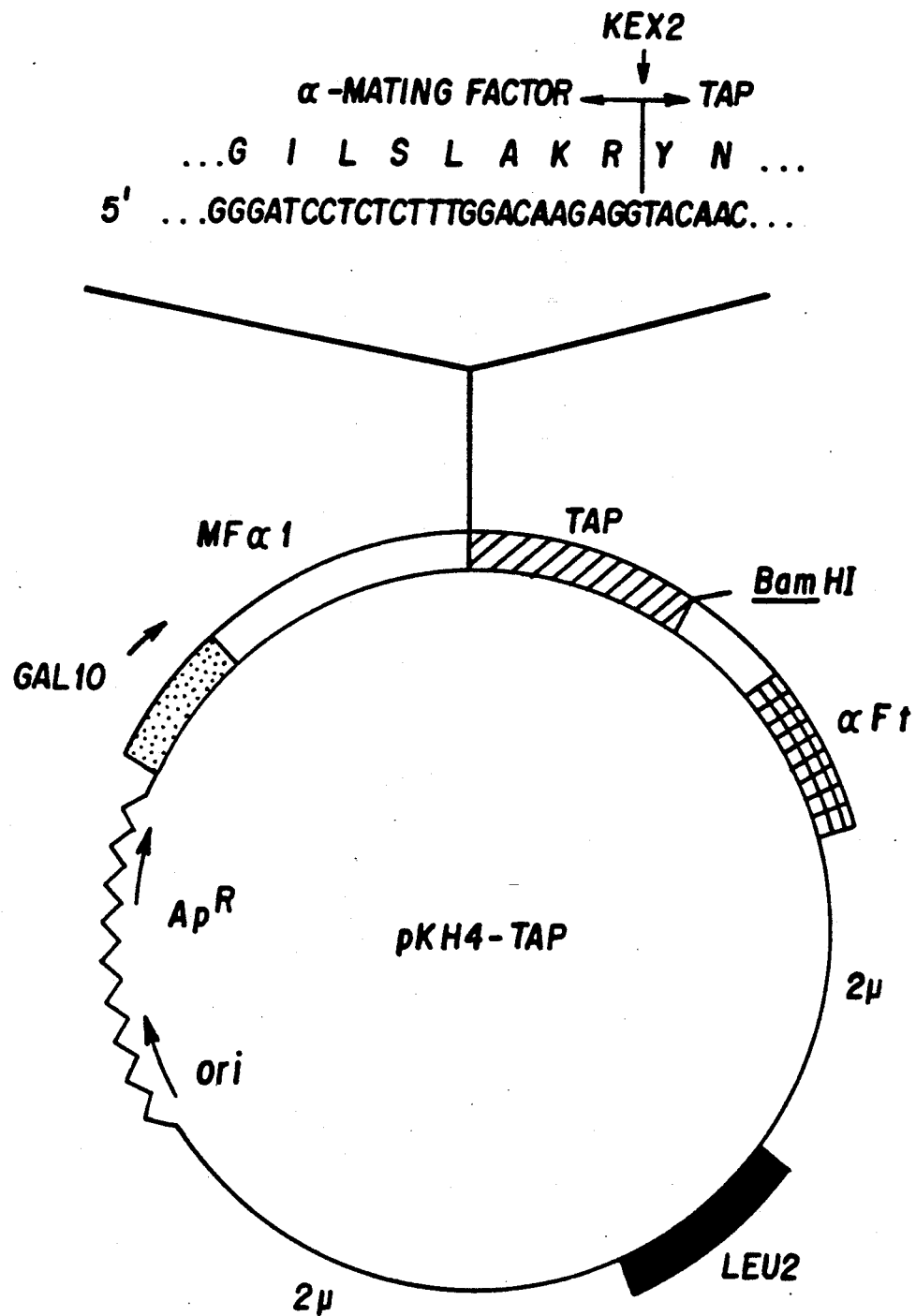
FIG. 4 shows insertion of α-mating factor•TAP gene to form pKH4•TAP, and specific identification of KEX2 processing site.

Polymerase chain reaction resulted in a blunt end fragment which was regenerated in the usual fashion by digestion with BamHI. The correct fragment was obtained after electrophoresis on a 2% agarose gel, excision of the band and electroelution. The purified fragment was ligated with the yeast expression vector pKH4α2 (Jacobson, M. A. et al. (1989) Gene 85: 513-518) that had been previously digested with BamHI and treated with calf alkaline phosphatase (FIG. 4). The correct sequence of plasmid clones in the correct orientation was confirmed by DNA sequence analysis. Fusion products produced from pKH4•TAP are proteolytically processed by the Lys-Arg-cleaving endopeptidase (KEX2) encoded by the KEX2 gene and products are secreted into culture medium. KEX2 cleaves on the C-terminal side of Lys-Arg residues.

Transformation of DMY6

Diploid yeast strain DMY6 (Schultz, L. D. (1987) Gene 61: 123-133) was transformed with pKH4•TAP using standard protocols (Hinnen et al. (1978) Proc. Natl. Acad. Sci. USA 75: 1929-1933). One isolate was chosen and designated S. cerevisiae MY 2030 9718P281-3. The isolate was deposited with the American Type Culture Collection and identified ATCC No. 20984.

From plate containing yeast transformants, single colony isolates were obtained. These isolates were grown in 5×CM leu medium (0.85% yeast nitrogen base without amino acids and ammonium sulfate, 1% succinic acid, 0.6% NaOH, 0.5% ammonium sulfate, 0.06% isoleucine, 0.06% phenylalanine, 0.04% lysine, 0.04% tryptophan, 0.025% tyrosine, 0.02% adenine, 0.02% uracil, 0.01% arginine, 0.01% histidine, 0.01% methionine, 0.04% FeCl$_3$.6H$_2$O, 0.03% ZnSO$_4$-7H$_2$O and 4% glucose) at 30° C. Cells were grown by inoculating a frozen stock culture of 281-3 on leucine-minus agar media for 3 days at 28° C. prior to the inoculation of 500 ml of selective medium (5×CM Leu−). The 500 ml seed culture was grown in a 2-1 Ehrlenmeyer flask for 16-18 hr at 28° C. using a rotary shaker at 300 rpm prior to its inoculation into 2.5 l of 5×CM Leu− broth containing 4% (w/v) galactose in a 1.5 l Bio-Flo III fermentor (New Brunswick Scientific). The fermentor was operated at 28° C., 900 rpm, 2.5 l/min air for 110-120 hr.

All work was done at 2°-8° C. Yeast cells were separated from broth (8 liters containing 1.69 gm. recombinant TAP-1) of yeast culture (strain 281-3) secreting recombinant TAP-1 by diafiltering the liquid through a 500,000 MWCO hollow fiber cartridge (Romicon, PM500, 5 ft) using an Amicon DC10 unit. The clarified broth was then diafiltered through a 100,000 MWCO hollow fiber cartridge (Amicon, H5P100-43) until approximately 500 mL of liquid remained in the reservoir. The retained liquid was diafiltered with 8 liters of 20 mM BIS-TRIS, pH 6.0. (Buffer A). The effluent of the 100,000 MWCO fibers was adjusted to pH 6.0 and diluted with 63 liters of cold buffer A. The diluted broth contained 1.67 gm of recombinant TAP-1. The diluted fermentation broth was divided into two 40 liter portions and wach was pumped at 2 liters/hr onto separate columns of Q-Sepharose Fast Flow ™ (Pharmacia: 14 cm × 10 cm I.D.) that had been equilibrated with buffer A. After all the diluted broth had been pumped onto the columns they were each washed with 8 liters of Buffer A to finish eluting unbound materials. The bound proteins were eluted with 16 liters linear gradient of 0-500 mM NaCl in Buffer A. Fractions of 400 mL were collected and monitored for $A_{280}$ and inhibition of human Factor Xa. Recombinant TAP-1 eluted at 175 mM NaCl.

The fractions that contained recombinant TAP-1 were combined and diluted with four volumes of 50 mM sodium acetate, pH 4.0 (Buffer B) before being pumped at 2 liters/hr onto a column of S-Sepharose Fast Flow ™ (Pharmacia; 24.5 cm × 7.5 cm I.D.) that had been equilibrated with Buffer B. When all the sample had been pumped onto the column it was washed with 8 liters of Buffer B and then the bound proteins were eluted with a 16 liters linear gradient of 0-400 mM NaCl in Buffer B. The fractions were monitored for $A_{280}$ and human Factor Xa inhibitory activity and recombinant TAP-1 eluted at 190 mM NaCl. The amount of recombinant TAP-1 eluted from the column was 1.58 gm. The pooled fractions containing inhibitory activity were loaded directly onto a 4.5 × 30 cm prep-pak $C_{18}$ HPLC column (Waters Associates) equilibrated with aqueous 0.1% (v/v) CF$_3$COOH at 50 ml/min using a Delta-Prep preparative HPLC system (Waters Assoc.). Following application of the sample at the same flow rate the column was washed with aqueous 0.1% (v/v) CF$_3$COOH for 5 min at 100 ml/min prior to the development of a CH$_3$CN gradient in aqueous 0.1% (v/v) CF$_3$COOH from 0-40% (v/v) at 1%/min. The peak of absorbance at 280 nm which eluted at a CH$_3$CN concentration of approximately 31% (v/v) was collected by hand and dried by lyophilization. Gel filtration chromatography can be used as an alternative to reserve phase HPLC to prepare desalted recombinant peptide. For gel filtration, Sephadex ™ G-10 (Pharmacia) was swollen in Milli-Q ™ H$_2$O and packed into a 2.5 cm (I.D.)×93 cm glass column and 90 mL of a solution of recombinant TAP-1 purified by S-Sepharose chromatography was chromatographed on it. Fractions of 12.5 mL were collected and monitored for $A_{280}$ and conductivity. Protein eluted in the $V_o$ and was well separated from the salt. The recovery of recombinant TAP-1 was 100%. The material was dried by lyophilization. The purified recombinant polypeptide prepared by either method was found to be greater than 99% pure by analytical reverse phase $C_{18}$ HPLC, quantitative amino acid analysis and automated amino-terminal sequence analysis. A typical specific content of the recombinant inhibitor was between 115 and 120 nmole/mg with a homogeneous amino-terminus beginning with tyrosine. The electrophoretic mobility of recombinant TAP-1 was identical to the native inhibitor as assessed sodium-dodecyl sulfate polyacrylamide gel electrophoresis under reducing conditions. The Factor Xa inhibitory activity of the recombinant TAP-1 was similar to that shown in FIG. 3 with a $K_i$ determined to be 0.2 nM.

Effectiveness of Recombinant TAP-1

An in vivo model of thromboplastin-induced clot formation similar to Van Ryn-McKenna, et al., (1989) *Thrombosis and Haemostasis* 61:7-9 was used to determine the efficacy of the Factor Xa inhibitor recombinant TAP-1. Rabbits were pretreated with an infusion of recombinant TAP-1 for 60 minutes, at which time a segment of the jugular vein was isolated and occluded. Thromboplastin and whole blood withdrawn from the carotid artery were injected into the segment in order to induce clot formation. The jugular vein remained occluded for 30 minutes before the clot was removed and quantitated.

Clot formation in rabbits receiving no anticoagulant pretreatment had normalized clot values of 29.2±3.4%. Clot formation with i.v. infusions of recombinant TAP-1 of 7 µg/kg/min, 37 µg/kg/min and 64 µg/kg/min were 27.0±7.5% and 7.9±2.0%, and 1.9±1.0% respectively. These doses did not significantly increase the activated partial thromboplastin time or prothrombin time.

TAP-1 MUTAGENESIS

Desired mutations of the TAP-1 open reading frame were prepared by one of two basic approaches: polymerase chain reaction mutagenesis, and Kunkel mutagenesis.

PCR Mutagenesis

The use of polymerase chain reaction catalyzed by Taq DNA polymerase for site-specific mutagenesis is described in Kadowaki et al., *Gene* 76 (1989) 161–166. Kadowaka et al. describe introduction of mismatches into the oligos used to prime polymerase chain reactions (Saiki, et al., *Science* 230 (1985) 1350–1354 and Saiki et al., *Science* 239 (1988) 487–491) in order to adopt the method to site-directed mutagenesis.

PCR Mutagenesis-Near-terminal location mutations

Mutations occurring near the ends of the TAP-1 coding sequence were modified through polymerase chain reaction (PCR) amplification of the TAP-1 template. Near-terminal location mutations include the TAP-1 mutation at residue position 53 which results in replacement of arginine with asparagine. By adding oligomer primers (complementary to the ends of the DNA to be amplified) to the TAP-encoding DNA and heating the reaction mixture, the DNA strands separate and permit annealling of the primers to the template. The primers bind opposite strands and, upon reaction with Taq polymerase (Cetus Perkin-Elmer) in a number of cycles of extension, strand separation and reannealling, the region between the primers is replicated. If one or more of the primers includes a mismatched region, that mutation is incorporated into the reaction product. TAP mutants were created through this amplification using the appropriate codon changes within the mutagenic primer. The PCR product was cleaved with BamH1, gel purified and then inserted into the pKH4α2 at the BamH1 site.

PCR Mutagenesis-Non-terminal location mutations

A modification of this approach was used for mutations desired at non-terminal location, occurring near unique Taq1 or Xho1 restriction sites: Non-terminal location mutations include the TAP-1 mutations at residue positions 9 and 23 which result in replacement of arginine with asparagine, and the TAP-1 mutations at residue position 16 which results in replacement of aspartic acid with arginine. Primers were prepared to amplify the TAP coding sequences and incorporate the mutations as before. The primers extended far enough to include restriction site sequences present in the TAP gene. Another set of primers were used to amplify remaining sequences of gene and the same restriction site. The resulting fragments were digested with that enzyme and ligated, reforming the TAP gene complete with the mutation. This material was purified and BamH1 digested for insertion in pKH4α2 as described above.

Kunkel Mutagenesis

Kunkel *Proc. Natl. Acad. Sci. U.S.A.* Vol. 82 (1985) 488–492, describes site-specific mutagenesis which takes advantage of a strong biological selection against the original, unaltered genotype. By using a relatively normal uracil-containing DNA template, prepared by standard procedures (Sagher and Strauss *Biochemistry* 22 (1983) 4518–4526) after growth on an *Escherichia coli* dut⁻ung⁻strain (Tye et al. *Proc. Natl. Acad. Sci. U.S.A.* 75 (1978) 233–237), site-specific mutagenesis procedures are used to produce mutations at high efficiencies without selection and in a few hours.

Mutants were prepared using a modification of the Kunkel method in which single strand p276-2E plasmid DNA was annealed with a complementary primer containing the desired mutagenic sequences. The Kunkel method was specifically employed to obtain a TAP-1 mutation at residue position 27 which results in replacement of arginine by asparagine. This complex was extended by DNA polymerase, covalently linked with DNA ligase and the product used to transform *E. coli* DH5 cells (Bethesda Research Laboratories). Mutation recovery was improved by selection against the parental strand using *E. coli* host CAG629 (dut-ung-BioRad) to prepare the singlestrand template. In presence of M13K07 helper phage (Pharmacia), one strand of the plasmid DNA is copied, packaged into phage capsids and secreted into the supernatant, permitting isolation of the single strand DNA. Because this strand contains uracil, it is degraded when the mutagenesis reaction mix is used to transform *E. coli* DH5(Dut+Ung+), leaving the mutagenized strand as template for replication. The modified TAP sequences were transferred as a BamH1 cassette to the pKH4α2 vector.

This method was also employed using the expression vector as the template for the mutagenesis reaction.

Therapy

The protein inhibits coagulation by inhibiting the Factor Xa pathway rather than by inhibition of thrombin. Factor Xa pathway inhibition is achieved by administering the protein, either by continuous intravenous administration or bolus administration, in combination with a suitable pharmaceutical composition carrier e.g. saline, at a suitable pH, e.g. 7.4, such that the composition achieves the desired effect of preventing Factor Xa from inducing formation of thrombin from prothrombin.

The proteinaceous substance of this invention having Factor $X_a$ inhibition activity can, like many proteins/peptides, form pharmaceutically acceptable salts with any non-toxic, organic or inorganic acid. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, trifluroacetic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Salts of the carboxy terminal amino acid moiety include the non-toxic carboxylic acid salts formed with any suitable inorganic or organic bases. Illustratively, these salts include those of alkali metals, as for example, sodium and potassium; alkaline earth metals, such as calcium and magnesium; light metals of Group IIIA including aluminium; and organic primary, secondary and tertiary amines, as for example, trialkylamines, including triethylamine, procaine, dibenzylamine, 1-ethenamine; N,N'-dibenzylethylenediamine, dihydroabietylamine, N-(lower)alkylpiperidine, and any other suitable amine.

The anticoagulant dose of the proteinaceous substance of this invention having Factor $X_a$ inhibition activity is from 0.2 mg/kg to 250 mg/kg of patient body weight per day depending on, for example, the patient, and the severity of the thrombotic condition to be treated. The suitable dose for a particular patient can be readily determined. Preferably from 1 to 4 daily doses would be administered typically with from 5 mg to 100 mg of active compound per dose. The concentration of the proteinaceous substance of this invention having Factor $X_a$ inhibition activity required to inhibit Factor $X_a$ when used to inhibit blood coagulation or Factor $X_a$ in a medium such as stored blood can be readily determined by those skilled in the art.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice. Inhibition of Factor $X_a$ is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the proteinaceous substance of this invention having Factor $X_a$ inhibition activity can be added to or contacted with any medium containing or suspected of containing Factor $X_a$ and in which it is desired that blood coagulation be inhibited.

Although the proteinaceous substance of this invention having Factor $X_a$ inhibition activity may survive passage through the gut following oral administration, applicants prefer non-oral administration, for example, subcutaneous, intravenous, intramuscular or intraperitoneal; administration by depot injection; or by implant preparation.

For parenteral administration the proteinaceous substance of this invention having Factor $X_a$ inhibition activity may be administered as injectable dosages of a solution or suspension of the substance in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solutions.

The proteinaceous substance of this invention having Factor $X_a$ inhibition activity can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The protein may be used alone or in combination with other proteins. For example, TAP enhances the efficiency of tissue plasminogen activator-mediated thrombolytic reperfusion. TAP may be administered first following thrombus formation, and tissue plasminogen activator or other plasminogen activator is administered thereafter.

Deposit

S. cerevisiae MY 2030 9718P281-3 deposited with the American Type Culture Collection, 12301 Parklawn Drive Rockville, Md. 20852, USA, is designated ATCC 20984. The deposit was made Feb. 21, 1990 under the provisions of the Budapest Treaty on the International Recognition of the Deposit of Microorganisms for the Purposes of Patent Procedure and the Regulations thereunder (Budapest Treaty). Maintenance of a viable culture is assured for 30 years from date of deposit. The organisms will be made available by ATCC under the terms of the Budapest Treaty, and subject to an agreement between Applicants and ATCC which assures unrestricted availability upon issuance of the pertinent U.S. patent. Availability of tye deposited strains is not to be construed as a license to practice the invention in contravention rights granted under the authority of any government in accordance with its patent laws.

What is claimed is:

1. A purified and isolated protein having the sequence:

$NH_2$—Tyr—Asn—Arg—Leu—Cys—Ile—Lys—Pro—

—$AA^9$—Asp—Trp—Ile[12]—

Asp—Glu—Cys—Asp—Ser—Asn—Glu—Gly—Gly—

-continued $$-\text{Glu}-\text{AA}^{23}-\text{Ala}-$$
$$\text{Tyr}-\text{Phe}-\text{AA}^{27}-\text{Asn}-\text{Gly}-\text{Lys}-\text{Gly}-\text{Gly}-\text{Cys}-$$
$$\text{Asp}-\text{Ser}-\text{Phe}-$$
$$\text{Trp}-\text{Ile}-\text{Cys}-\text{Pro}-\text{Glu}-\text{Asp}-\text{His}-\text{Thr}-\text{Gly}-$$
$$-\text{Ala}-\text{Asp}-\text{Tyr}-$$
$$\text{Tyr}-\text{Ser}-\text{Ser}-\text{Tyr}-\text{AA}^{53}-\text{Asp}-\text{Cys}-\text{Phe}-\text{Asn}-$$
$$-\text{Ala}-\text{Cys}-\text{Ile}-\text{COOH}$$

wherein
$AA^9$ is Arg or Asn,
$AA^{23}$ is Arg or Asn,
$AA^{27}$ is Arg or Asn, and
$AA^{53}$ is Arg or Asn.

2. A protein of claim 1, wherein $AA^9$ is Arg, $AA^{23}$ is Arg, $AA^{27}$ is Arg, and $AA^{53}$ is Arg.

3. A protein of claim 1, wherein $AA^9$ is Asn, $AA^{23}$ is Arg, $AA^{27}$ is Arg, and $AA^{53}$ is Arg.

4. A protein of claim 1, wherein $AA^9$ is Arg, $AA^{23}$ is Arg, $AA^{27}$ is Arg, and $AA^{53}$ is Arg.

5. A protein of claim 1, wherein $AA^9$ is Arg, $AA^{23}$ is Arg, $AA^{27}$ is Asn, and $AA^{53}$ is Arg.

6. A protein of claim 1, wherein $AA^9$ is Arg, $AA^{23}$ is Arg, $AA^{27}$ is Arg, and $AA^{53}$ is Asn.

7. A therapeutic composition for inhibiting blood coagulation Factor Xa comprising an effective amount of the protein of claim 1 and a pharmaceutically-acceptable carrier.

8. A method for inhibiting blood coagulation Factor Xa in a mammal comprising administering to the mammal an effective dose of a composition of claim 7.

9. A method for achieving thrombolytic reperfusion following thrombus formation in a patient comprising administering a protein of claim 1 to inhibit Factor Xa and thereafter administering tissue plasminogen activator or other plasminogen activator.

* * * * *